(12) United States Patent
Wolcott et al.

(10) Patent No.: US 8,365,616 B1
(45) Date of Patent: Feb. 5, 2013

(54) SAMPLING PROBE FOR SOLUTIONS CONTAINING SOLUBLE SOLIDS OR HIGH CONCENTRATIONS OF DISSOLVED SOLIDS

(76) Inventors: Duane K. Wolcott, Fox Island, WA (US); Graham D. Marshall, Fox Island, WA (US)

( * ) Notice: Subject to any disclaimer, the term of this patent is extended or adjusted under 35 U.S.C. 154(b) by 295 days.

(21) Appl. No.: 12/883,775

(22) Filed: Sep. 16, 2010

(51) Int. Cl.
- G01N 1/26 (2006.01)
- G01N 1/16 (2006.01)
- G01N 1/00 (2006.01)

(52) U.S. Cl. ............ 73/863.33; 73/863; 73/863.31

(58) Field of Classification Search .......... 73/23.41, 73/61.56, 64.56, 863, 863.31, 863.33, 864.21, 73/864.22, 864.73, 864.81
See application file for complete search history.

(56) References Cited

U.S. PATENT DOCUMENTS

| | | | |
|---|---|---|---|
| 3,954,411 A | 5/1976 | Snyder | |
| 4,379,402 A * | 4/1983 | Harman, III | 73/23.21 |
| 4,826,775 A | 5/1989 | Burns et al. | |
| 5,411,708 A | 5/1995 | Moscetta | |
| 5,695,720 A | 12/1997 | Wade et al. | |
| 5,884,488 A * | 3/1999 | Gram et al. | 62/50.6 |
| 6,334,312 B1 * | 1/2002 | Mack et al. | 62/50.1 |
| 6,426,225 B1 | 7/2002 | Lewis et al. | |
| 7,247,487 B2 | 7/2007 | Jacobs et al. | |
| 7,416,896 B1 | 8/2008 | Ahlfors et al. | |
| 8,261,780 B2 * | 9/2012 | Thomas et al. | 141/9 |
| 2003/0013200 A1 | 1/2003 | Pai et al. | |
| 2005/0053522 A1 | 3/2005 | King et al. | |
| 2005/0207941 A1 | 9/2005 | Lee et al. | |
| 2005/0244299 A1 * | 11/2005 | Dasgupta et al. | 422/68.1 |
| 2009/0147822 A1 * | 6/2009 | Tokhtuev et al. | 374/142 |

* cited by examiner

*Primary Examiner* — Hezron E Williams
*Assistant Examiner* — David Z Huang
(74) *Attorney, Agent, or Firm* — Reginald F. Roberts, Jr.

(57) ABSTRACT

An analytical system for solutions containing soluble solids or high concentrations of dissolved solids. The system includes a container having upper and lower portions; a lead an/or a tubing line extending into the upper portion of the container, for withdrawing a portion of a gas in the upper portion of the container; and a sampling probe extending into the lower portion of the container, for withdrawing a portion of a sample of a liquid or of a mixture of a liquid and a solid. The sampling probe is a probe support shaft which may be provided with a filter for separating liquid and solid phases from one another if the sample is a liquid-solid mixture. Gas in the headspace above the liquid or the liquid-solid mixture can be withdrawn through the lead and/or the tubing line.

4 Claims, 2 Drawing Sheets

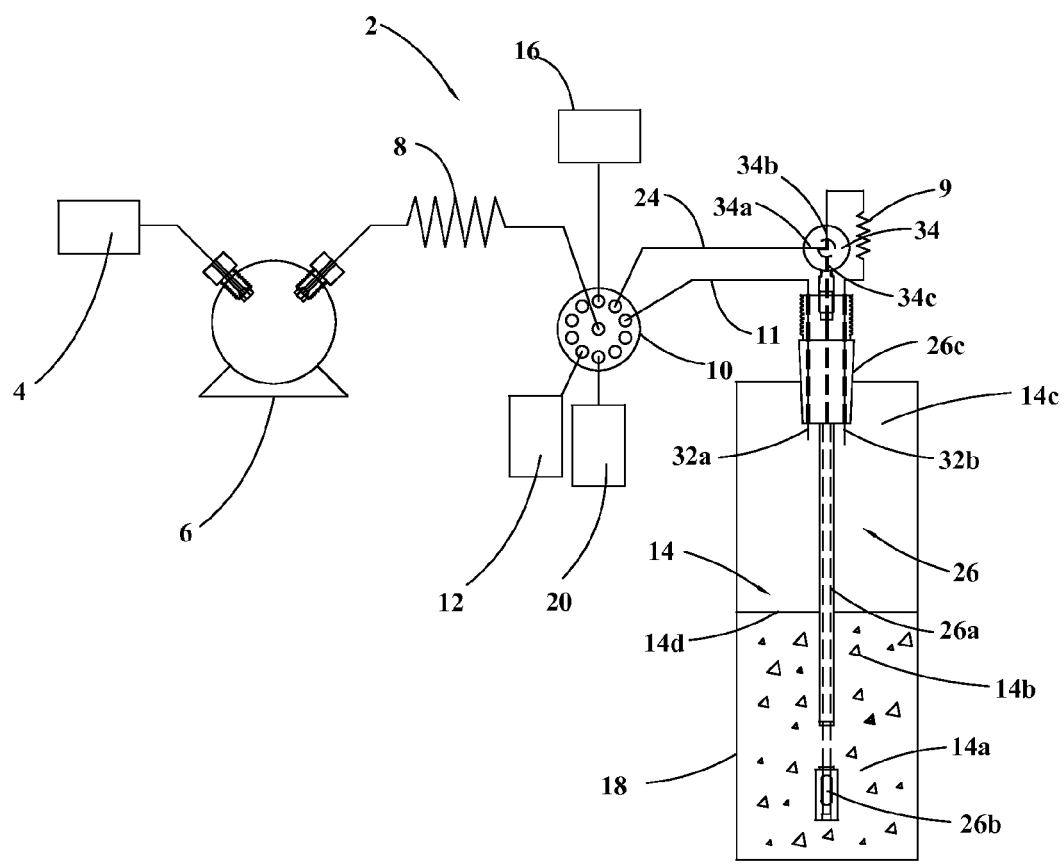
FIGURE 1-A

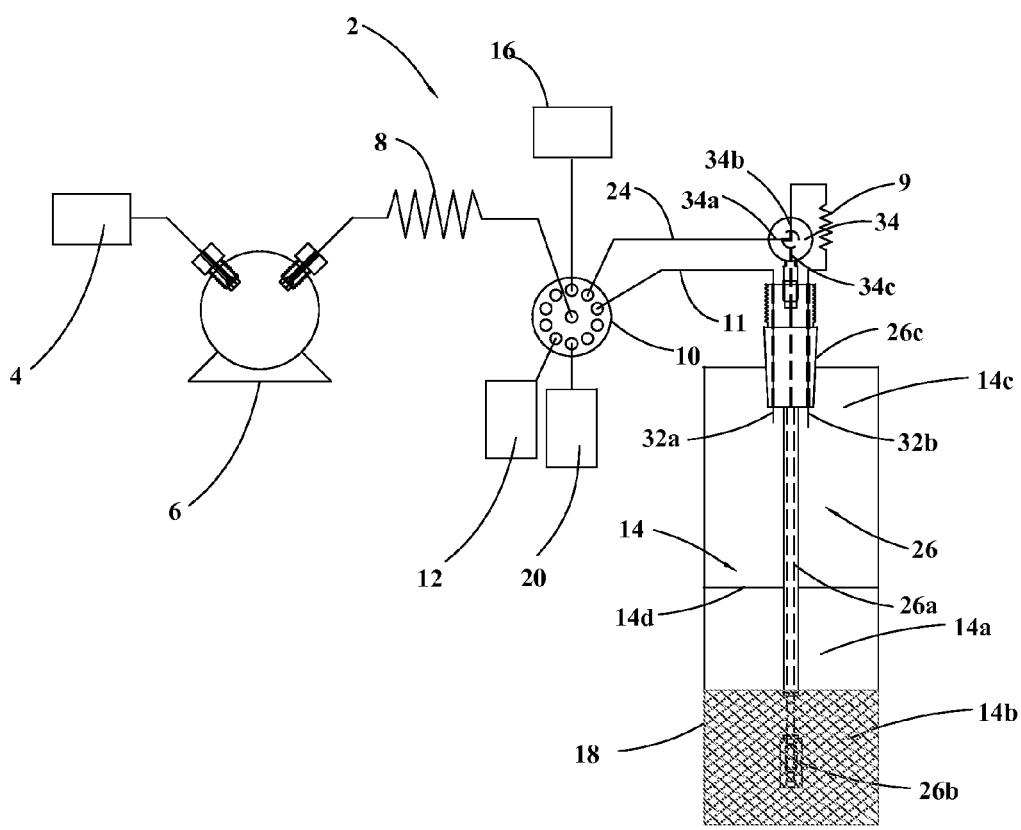
FIGURE 1-B

SAMPLING PROBE FOR SOLUTIONS CONTAINING SOLUBLE SOLIDS OR HIGH CONCENTRATIONS OF DISSOLVED SOLIDS

BACKGROUND OF THE INVENTION

The present invention relates to instrumental chemical analysis. More particularly, the invention relates to an apparatus and a method for sampling solutions containing soluble solids or high concentrations of dissolved solids.

Many manufacturing processes operate at elevated temperatures so that reactants and/or products at concentrations above the ambient solubility of the compound can be used. This method has obvious financial and environmental advantages. Furthermore, processes often produce a product or use a reactant that may be insoluble in one solvent but quite soluble in another solvent. Diluting the solid sample in the more favorable solvent produces a sample in solution which is easier to handle during analysis than the solid. In still other processes it is desirable to exclude the solid fraction in the process and simply sample the liquid phase.

Some existing sampling strategies make use of costly heat tracing to maintain the temperature of the sample to prevent it from precipitating from solution as the solution cools. Other systems employ various filtering strategies to exclude solids, but these filtering devices are seldom amenable to conversion into a device that will allow sampling of processes with high concentrations of dissolved or undissolved solids, or where the solid fraction is required to be sampled as well.

SUMMARY OF THE INVENTION

In general, the present invention in a first aspect provides an analytical system for solutions containing soluble solids or high concentrations of dissolved solids. The analytical system comprises (a) a container having upper and lower portions; (b) means for sampling a gas disposed in the upper portion of the container; and (c) means for sampling a liquid or a mixture of a liquid and a solid disposed in the lower portion of the container.

A first embodiment of the analytical system comprises (a) a container having upper and lower portions; (b) a lead extending into the upper portion of the container, for withdrawing a portion of a gas disposed therein; and (c) a sampling probe extending into the lower portion of the container, for withdrawing a portion of a sample of a liquid or of a mixture of a liquid and a solid.

A second embodiment of the analytical system comprises (a) a multi-port selection valve; (b) a container having upper and lower portions; (c) a lead having first and second ends, the first end of the lead extending into the upper portion of the container, the second end of the lead being connected to the multi-port selection valve, for transferring a portion of a gas disposed in the upper portion of the container to the selection valve; and (d) a sampling probe extending into the lower portion of the container, for transferring a portion of a sample of a liquid or of a mixture of a liquid and a solid disposed in the lower portion of the container to the selection valve.

In a second aspect, the invention provides a sampling probe for samples comprising a mixture of a liquid and a solid. The sampling probe comprises (a) a probe support shaft; and (b) a filter, for separating the liquid and the solid in the mixture from one another before transporting the liquid, the solid, or the liquid and the solid through the tubing.

In a third aspect, the invention provides a method for sampling a gas, a liquid, or a mixture of a liquid and a solid. The method comprises (a) disposing the gas and the liquid, or the gas and the mixture of the liquid and the solid in a closed container, so that the gas occupies space above the liquid or above the mixture of the liquid and the solid; (b) disposing a tubing line or a lead in the space above the liquid or above the mixture of the liquid and the solid; (c) disposing a sampling probe beneath surface of the liquid or the mixture of the liquid and the solid; (d) disposing a selection valve in close proximity to the container; (e) connecting the tubing line or the lead and the sampling probe to the selection valve, to enable selection of either a portion of the gas, or a portion of the liquid or of the mixture of the liquid and the solid to be transferred to the selection valve; and (f) transferring the portion of the gas, the portion of the liquid, or the portion of the mixture of the liquid and the solid from the container to the selection valve, thereby obtaining a sample of the gas, of the liquid, or of the mixture of the liquid and the solid.

BRIEF DESCRIPTION OF THE DRAWINGS

FIGS. 1-A and 1-B are schematic representations of an analytical system made in accordance with the principles of the present invention.

DETAILED DESCRIPTION OF THE DISCLOSED EMBODIMENTS

The present invention provides a robust and convenient means of sampling manufacturing processes that operate at temperatures above the ambient solubility of reactants and/or products, processes that generate a product or use a reactant that may be insoluble in one solvent but quite soluble in another solvent, or processes in which it is desirable to exclude a solid phase while sampling a liquid phase.

A sample probe is equipped with a multi-port valve having a minimum of three ports, in close proximity to the sampling point. The multi-port valve may be a solenoid valve, but is preferably a rotary valve. The common port of the multi-port valve is coupled via a multi-port selection valve to a fluid-propelling device. One of the selection ports is coupled to the sampling probe. Another port of the multi-port valve is coupled to the head space above the process to be sampled. The multi-port valve allows for the sample zone to be sandwiched between two solvent zones. The sample is diluted and mixed with the solvent in close proximity to the sample point. This design also allows the resultant solvent-sample-solvent stack to be conveniently sandwiched between gas bubbles drawn from the headspace of the process being sampled or drawn from the ambient environment. The sampling probe can be equipped with either a filter element or a solids inlet, depending on whether or not the solids are to be excluded from the sample, so that the probe can be easily transformed from a heterogeneous sampler to a filtering sampler.

More specifically, reference is made to FIGS. 1-A and 1-B, in which are shown an analytical system, made in accordance with the principles of the present invention, and generally designated by the numeral 2.

The analytical system 2 comprises a source of a carrier 4, a bi-directional pump 6 for propelling fluids through the sampling system 2, a multi-port selection valve 10, a first holding coil 8 connecting the pump 6 to a central first port of the selection valve 10, a reservoir of solvent 12, 20 connected to second and third ports of the selection valve 10, a second holding coil 9, a container 18 for a sample 14, a multi-port valve 34 connecting the container 18 via a segment of tubing 24 to a fourth port of the multi-port selection valve 10, and a detector 16 connected to a fifth port of the multi-port selection valve 10.

The pump 6 is a high-precision, bi-directional, positive-displacement pump.

The multi-port valve 34 comprises a common first port 34a, a second port 34b, and a third port 34c. Preferably, the multi-port valve 34 includes a plurality of other ports, which may be employed as desired or as needed for sampling and analysis. A sampling probe 26 extends into the container 18 through the headspace 14c above the surface 14d of the sample 14 into the sample 14. A tubing line probe 32a extends into the headspace 14c above the surface 14d of the sample 14. The sample 14 may comprise a liquid phase 14a and a solid phase 14b. If both phases are present, the sample 14 may be a slurry of solids 14b suspended in a liquid 14a, as represented by FIG. 1-A, or the two phases may exist as two distinct layers of liquid 14a and solids 14b, as depicted in FIG. 1-B.

The sampling probe 26 comprises a probe support shaft 26a, and may further comprise a filter 26b. If the sample 14 comprises only a liquid phase 14a, the sampling probe 26 is simply the probe support shaft 26a. If both liquid 14a and solid 14b phases constitute the sample 14, and the objective is to sample both phases, the sampling probe 26 again comprises only the probe support shaft 26a. If the objective is to sample only the liquid 14a and to exclude the solids 14b, then the sampling probe 26 comprises both the probe support shaft 26a and the filter 26b. The sampling probe 26 is connected to the multi-port valve 34 by a body 26c. The common first port 34a of the multi-port valve 34 is coupled via the selection valve 10 and the first holding coil 8 to the pump 6. The second port 34b of the multi-port valve 34 is coupled to the second holding coil 9. The third port 34c of the multi-port valve 34 is connected to the sampling probe 26. A lead 32b from the second holding coil 9 extends into the headspace 14c of the container 18. The tubing line 32a extending into the headspace 14c is coupled directly to the multi-port selection valve 10 by a segment of tubing 11, thereby enabling direct access to the contents of the headspace 14c.

The analytical system 2 is operated in the following manner.

If the contents of the container 18 to be sampled is all liquid phase, but the sample 14 contains reaction products which will precipitate if the temperature is reduced below that in the container 18, the sample probe 26 comprises the probe support shaft 26a. A zone of solvent 20 is aspirated by the pump 6 into the first holding coil 8, then transferred into the tubing line 24. The zone of solvent 20 is trailed by a bubble from the headspace 14c which has been drawn into the first holding coil 8 through the tubing line 11. The function of the trailing bubble is to minimize mixing between the carrier 4 and the solvent 20, if these are not the same liquid. The multi-port valve 34 is switched to the second holding coil 9 attached to the second port 34b, and a portion of the solvent zone is positioned in the second holding coil 9. The multi-port valve 34 is switched to the sampling probe 26, and a portion of the solvent 20 is pushed down into the sampling probe 26, but not so far as to be pushed out of the end of the sampling probe 26. At this point, an aliquot of sample 14 is drawn from the container 18 into the sampling probe 26 and into line 24. The portions of the solvent 20 preloaded into the sampling probe 26 and remaining in line 24 assure that any shift in temperature that might cause precipitation occurs in a solvent medium such that the concentration of sample 14 plus solvent 20 is always below the precipitation point. Once the desired aliquot volume of sample 14 has been drawn up into the sampling probe 26 and line 24, flow is stopped, and the multi-port valve 34 is switched to port 34b. Flow is then restarted, and the solvent 20 and sample 14 volume, including the solvent 20 aliquot preloaded into the second holding coil 9, is drawn into the first holding coil 8. As the solvent-sample-solvent zone stack is withdrawn, the volume of gas in and between the second holding coil 9 and the headspace port 34b results in the solvent-sample-solvent stack being "bubble bounded," i.e., has a leading and trailing bubble between the zone stack and the carrier/solvent. The condition of being "bubble bounded" results in Taylor flow within the zone stack, whereby highly efficient mixing takes place within the zone stack. Because the flow rate at the center of the tube is faster than at the walls, and the liquid zone is constrained by bubbles, a circular flow pattern is established that promotes mixing of the elements in the mixing zone. Passage of the solvent 20 aliquot preloaded into the second holding coil 9 through the multi-port valve 34 assures thorough washout of the internals of the multi-port valve 34, thereby preventing any buildup of solids that might cause blockage.

If the contents of the container 18 is a mixture of liquid and solid, and the desired goal is to analyze both phases, a sequence of fluidic actions identical to the above are performed. Care is taken to use a solvent and solvent-to-sample ratio such that all solids are completely dissolved by the time the sample-solvent-bubble-bounded zone reaches the first holding coil 8.

If the contents of the container 18 is a mixture of liquid and solid, and the desired goal is to analyze only the liquid portion, the sampling probe 26 is terminated with the filter element 26a. A series of fluidic manipulations identical to that described above are carried out. In this instance, the step of pushing a solvent aliquot back into the probe support shaft 26a through the second port 34b also performs the useful function of back-flushing the filter 26a.

It will be apparent to those skilled in the art that the present invention provides an analytical system for and a method of sampling solutions containing soluble solids or high concentrations of dissolved solids having many advantages over the prior art. While the following features illustrate some of these advantages, they are by no means a complete or exhaustive listing of the possibilities inherent in the present invention.

(a) A means of carrying out a dilution in close proximity to the sample point in such a way that carryover is minimized.

(b) A probe that is easily transformed from a heterogeneous sampler to a filtering sampler.

(c) A convenient means of utilizing headspace gas for bracketing bubbles. This feature is particularly important where the material being sampled is sensitive to air, e.g. is easily oxidized. Use of an inert gas such as nitrogen in the headspace solves this problem.

(d) A simple device for handling samples at elevated temperatures and/or at concentrations above their ambient-temperature saturation point, samples at ambient temperatures close to their saturation point, and heterogeneous samples that are easily solubilized with an appropriate solvent.

There are several advantages to sampling a process and carrying out a primary dilution step in close proximity to the sampling point, in accordance with the principles of the present invention:

The concentration of the sample can be lowered below its ambient temperature solubility point before there is opportunity to clog narrow-bore tubing through which the sample is transported.

A heterogeneous sample can be solubilized by employing a suitable solvent as the diluent.

A finely-divided heterogeneous sample can be transported, through narrow-bore tubing, bracketed between suitable liquids and/or gas bubbles.

A wash solution can be pre-positioned to flush homogeneous or heterogeneous samples from behind the sample zone without contaminating the process with the wash solution.

If required, bracketing gas zones can be drawn from the headspace of the process, thus protecting the sample from being exposed to other gases with which the sample may be incompatible.

The sampling probe 26 has the advantage that it is a simple operation to exchange the tip from a solids inlet to a filter cartridge, depending on sample requirements.

In addition to all of the advantages described above, it will be apparent to the skilled artisan that the present invention has the tremendous and unique advantage of being adaptable to and suitable for sampling both liquid and gaseous phases of a process taking place in a chemical reactor. Other advantageous adaptations and uses of the invention will occur to those skilled in the art.

While certain specific details and embodiments have been described to illustrate the principles of the present invention, it will be apparent to those skilled in the art that many modifications are possible within the scope of the disclosed invention.

We claim:

1. An analytical system, comprising:
    (a) a container having upper and lower portions;
    (b) a lead extending into the upper portion of the container, for withdrawing a portion of a gas disposed therein;
    (c) a sampling probe extending into the lower portion of the container, for withdrawing a portion of a sample of a liquid or of a mixture of a liquid and a solid disposed therein;
    (d) a multi-port selection valve, in close proximity to the container and to the sampling probe, for receiving a portion of the gas or of the sample, for diluting a sample in close proximity to the sampling probe, and for disposing a sample between successive portions of a diluent;
    (e) a multi-port valve connecting the lead and the sampling probe to the selection valve, for selecting either the gas portion or the sample portion to be transferred to the port of the selection valve; and
    (f) a source of diluent connected to the selection valve, for diluting the sample as required.

2. An analytical system, comprising:
    (a) a container having upper and lower portions;
    (b) a lead extending into the upper portion of the container, for withdrawing a portion of a gas disposed therein;
    (c) a sampling probe extending into the lower portion of the container, for withdrawing a portion of a sample of a liquid or of a mixture of a liquid and a solid disposed therein;
    (d) a multi-port selection valve for receiving a portion of the gas or of the sample;
    (e) a multi-port valve connecting the lead and the sampling probe to the selection valve, for selecting either the gas portion or the sample portion to be transferred to the port of the selection valve; and
    (f) a detector connected to the selection valve, for determining concentration of a constituent of the sample.

3. An analytical system, comprising:
    (a) a container having upper and lower portions;
    (b) a lead extending into the upper portion of the container, for withdrawing a portion of a gas disposed therein;
    (c) a sampling probe extending into the lower portion of the container, for withdrawing a portion of a sample of a liquid or of a mixture of a liquid and a solid disposed therein;
    (d) a multi-port selection valve for receiving a portion of the gas or of the sample;
    (e) a multi-port valve connecting the lead and the sampling probe to the selection valve, for selecting either the gas portion or the sample portion to be transferred to the port of the selection valve; and
    (f) a source of diluent connected to the selection valve, for diluting the sample as required.

4. An analytical system, comprising:
    (a) a container having upper and lower portions;
    (b) a lead extending into the upper portion of the container, for withdrawing a portion of a gas disposed therein;
    (c) a sampling probe extending into the lower portion of the container, for withdrawing a portion of a sample of a liquid or of a mixture of a liquid and a solid disposed therein;
    (d) a multi-port selection valve for receiving a portion of the gas or of the sample;
    (e) a multi-port valve connecting the lead and the sampling probe to the selection valve, for selecting either the gas portion or the sample portion to be transferred to the port of the selection valve;
    (f) a bi-directional pump, for transporting a portion of the gas, a portion of the sample, a portion of the diluent, and/or a portion of a carrier liquid through the sampling system; and
    (g) a holding coil connecting the pump to the selection valve.

* * * * *